United States Patent [19]

Fukui et al.

[11] 4,363,916
[45] Dec. 14, 1982

[54] HYDANTOIN DERIVATIVES

[75] Inventors: Kiyoshi Fukui; Noboru Kakeya; Hiroshi Jibiki; Junichiro Kita, all of Ichihara, Japan

[73] Assignee: Ube Industries, Ltd., Ube, Japan

[21] Appl. No.: 306,964

[22] Filed: Sep. 30, 1981

[30] Foreign Application Priority Data

Oct. 9, 1980 [JP] Japan ................................ 55/140406

[51] Int. Cl.³ ........................................... C07D 233/78
[52] U.S. Cl. .................................................. 548/313
[58] Field of Search ......................................... 548/313

[56] References Cited

U.S. PATENT DOCUMENTS 4,062,847 12/1977 Rambacher et al. ................ 548/313

FOREIGN PATENT DOCUMENTS 39-19804 12/1964 Japan .

Primary Examiner—Robert W. Ramsuer
Attorney, Agent, or Firm—Frishauf, Holtz, Goodman & Woodward

[57] ABSTRACT

Hydantoin derivatives disclosed in the present application are represented by the formula

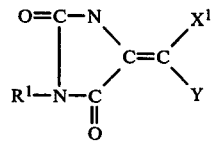

wherein, $R^1$ represents a hydrogen atom, an alkyl group of from 1 to 4 carbon atoms, an allyl group, a cyclohexyl group, a benzyl group or a group

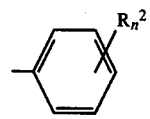

(where $R^2$ is an alkyl group of from 1 to 4 carbon atoms, an alkoxy group of from 1 to 4 carbon atoms, a halogen atom or a nitro group, and n is 0, 1, 2 or 3), $X^1$ is an alkoxycarbonyl group of from 2 to 5 carbon atoms, a benzoyl group, an aliphatic acyl group of from 2 to 5 carbon atoms or a cyano group, and Y is an alkoxycarbonyl group of from 2 to 5 carbon atoms or an aliphatic acyl group of from 2 to 5 carbon atoms. The hydantoin derivatives are useful as agricultural chemicals e.g. bactericides or intermediates thereof.

4 Claims, No Drawings

HYDANTOIN DERIVATIVES

The present invention relates to novel hydantoin derivatives.

As hydantoin derivatives, there have hitherto been known compounds represented by the formula

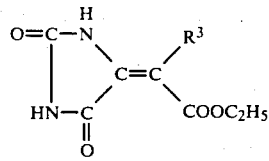

wherein $R^3$ is a hydrogen atom, a lower alkyl group, an allyl group, a halogen atom or a nitro group, and a compound represented by the formula

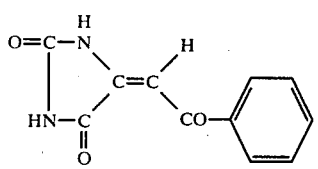

It is an object of the present invention to provide novel hydantoin derivatives which are useful as agricultural chemicals or intermediates thereof.

The present invention provides novel hydantoin derivatives represented by the formula I

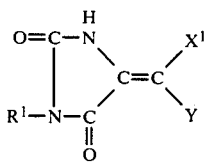

where $R^1$ is a hydrogen atom, an alkyl group of from 1 to 4 carbon atoms, an allyl group, a cyclohexyl group, a benzyl group or a group

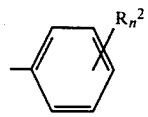

(where $R^2$ is an alkyl group of from 1 to 4 carbon atoms, an alkoxyl group of from 1 to 4 carbon atoms, a halogen atom or a nitro group, and n is 0, 1, 2 or 3), $X^1$ represents an alkoxycarbonyl group of from 2 to 5 carbon atoms, a benzoyl group, an aliphatic acyl group of from 2 to 5 carbon atoms or a cyano group, and Y represents an alkoxycarbonyl group of from 2 to 5 carbon atoms or an aliphatic acyl group of from 2 to 5 carbon atoms.

The hydantoin derivatives represented by the formula I are useful as agricultural chemicals or intermediates thereof.

The hydantoin derivatives represented by the formula I can be synthesized by the following methods 1 to 4.

1. An ester of an α-amino acid represented by the formula II

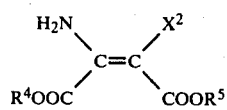

where each of $R^4$ and $R^5$, represents an alkyl group of from 1 to 4 carbon atoms, and $X^2$ represents an alkoxycarbonyl group of from 2 to 5 carbon atoms, a benzoyl group or a cyano group, is reacted with phosgene or trichloromethyl chloroformate in the presence of pyridine, and then the reaction product is reacted with a primary amine represented by the formula $R^1NH_2$ wherein $R^1$ is as defined above.

In this reaction, if an alkylamine, cyclohexylamine, allylamine, benzylamine or an alkoxyaniline is used as the primary amine, a precursor of the hydantoin derivative represented by the formula

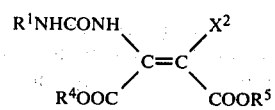

where $R^1$, $R^4$, $R^5$ and $X^2$ are as defined above, is obtainable in certain cases, as well as the hydantoin derivative. In such a case, it is possible to convert the above ester of hydantoic acid to the hydantoin derivative by adding a tertiary amine such as triethylamine, tripropylamine or tributylamine to the reaction product mixture or to the ester of hydantoic acid isolated from the reaction product mixture, and heating the mixture thereby obtained, to effect the ring closure of the ester.

2. An ester an α-amino acid represented by the formula III

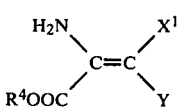

where $R^4$, $X^1$ and Y are as defined above, is reacted with an isocyanate represented by the formula IV $R^6-N=C=O$      IV wherein $R^6$ is an alkyl group of from 1 to 4 carbon atoms, an allyl group, a cyclohexyl group, a benzyl group or a group

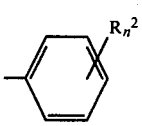

(where $R^2$ and n are as defined above), in the presence of a quaternary ammonium fluoride.

3. An ester of an α-amino acid represented by the formula V

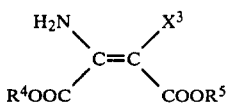

wherein $R^4$ and $R^5$ are as defined above, and $X^3$ represents an alkoxycarbonyl group of from 2 to 5 carbon atoms, an acetyl group or a benzoyl group, is reacted with an aromatic isocyanate represented by the formula VI

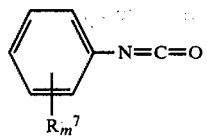

where $R^7$ represents an alkyl group of from 1 to 4 carbon atoms, an alkoxy group of from 1 to 4 carbon atoms or a halogen atom, and m is 0, 1, 2 or 3 in the presence of a metal of Group IA or a hydride of a metal of Group IA or Group IIIA.

4. The ester of an α-amino acid represented by the formula III is reacted with the aromatic isocyanate represented by the formula VI in the presence of a tertiary amine.

Each of the above reactions may be carried out normally at a temperature within a range of from 20° to 100° C. in the absence or presence of a reaction solvent, for instance, an aromatic hydrocarbon such as benzene or toluene, a halogenated hydrocarbon such as dichloromethane, chloroform or chlorobenzene, or an ether such as diethyl ether, dibutyl ether or tetrahydrofuran.

Esters of α-amino acids represented by the formula II, III or V may be synthesized, for instance, by the following methods:

1. An ester of cyanoformic acid represented by the formula $N\equiv C-COOR^4$ is reacted with an active methylene compound represented by the formula,

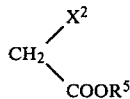

the formula,

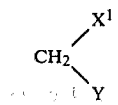

or the formula

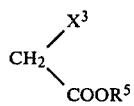

in the presence of a halide of titanium or tin, and the reaction product mixture is treated with water or an aqueous acidic solution (see Japanese Patent Provisional Publication No. 103143/1981 filed by the present applicant).

2. A compound represented by the formula

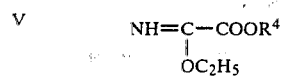

is reacted with the above mentioned active methylene compound.

In each of the above formulas, $X^1$, $X^2$, $X^3$, $R^4$ and $R^5$ are the same as defined with respect to formulas II to V.

Now, specific examples of the hydantoin derivatives of the present invention and their melting points will be given as follows:

| Nos. | Hydantoin Derivatives | Melting Points (°C.) |
|---|---|---|
| 1 | 5-bis(ethoxycarbonyl)methylene-3-isopropylhydantoin | 101 to 103 |
| 2 | 5-bis(ethoxycarbonyl)methylene-3-(n-butyl)hydantoin | 59 to 61 |
| 3 | 5-bis(ethoxycarbonyl)methylene-3-allylhydantoin | 91 to 92 |
| 4 | 5-bis(ethoxycarbonyl)methylene-3-cyclohexylhydantoin | 118 to 121 |
| 5 | 5-bis(ethoxycarbonyl)methylene-3-benzylhydantoin | 149 to 151 |
| 6 | 5-bis(ethoxycarbonyl)methylene-3-phenylhydantoin | 167.5 |
| 7 | 5-bis(ethoxycarbonyl)methylene-3-(p-tolyl)hydantoin | 154 to 155 |
| 8 | 5-bis(ethoxycarbonyl)methylene-3-(p-chlorophenyl)hydantoin | 161.5 to 162 |
| 9. | 5-bis(ethoxycarbonyl)methylene-3-(2,5-dichlorophenyl)hydantoin | 178 to 179 |
| 10. | 5-bis(ethoxycarbonyl)methylene-3-(3,5-dichlorophenyl)hydantoin | 172 to 175 |
| 11. | 5-bis(ethoxycarbonyl)methylene-3-(2,4,5-trichlorophenyl)hydantoin | 172 to 174 |
| 12. | 5-bis(ethoxycarbonyl)methylene-3-(2-methoxy-4-nitrophenyl)hydantoin | 170 to 172 |
| 13. | 5-bis(methoxycarbonyl)methylene-3-isopropylhydantoin | 128 to 129 |
| 14. | 5-bis(methoxycarbonyl)methylene-3-benzylhydantoin | 169 to 171 |
| 15. | 5-bis(methoxycarbonyl)methylene-3-(3,5-dichlorophenyl)hydantoin | 228 to 230 |
| 16. | 5-bis(methoxycarbonyl)methylene-3-(p-anisyl)hydantoin | 204 to 206 |
| 17. | 5-(benzoyl) (ethoxycarbonyl)methylene-3-isopropylhydantoin | 160 to 162 |
| 18. | 5-(benzoyl) (ethoxycarbonyl)methylene-3-(n-butyl)hydantoin | 142 to 144 |
| 19. | 5-(benzoyl) (ethoxycarbonyl)methylene-3-allylhydantoin | 176 to 178 |
| 20. | 5-(benzoyl) (ethoxycarbonyl)methylene-3-cyclohexylhydantoin | 184 to 186 |
| 21. | 5-(benzoyl) (ethoxycarbonyl)methylene-3-phenylhydantoin | 213 to 214 |
| 22. | 5(benzoyl) (ethoxycarbonyl)methylene-3-(p-tolyl)hydantoin | 205 to 206 |
| 23. | 5-(benzoyl) (ethoxycarbonyl)methylene-3-(3,4-xylyl)hydantoin | 195 to 197 |
| 24. | 5-(benzoyl) (ethoxycarbonyl)methylene-3-(2,5-dichlorophenyl)hydantoin | 140 to 141 |
| 25. | 5-(benzoyl) (ethoxycarbonyl)methylene-3-(3,5-dichlorophenyl)hydantoin | 249 to 251 |
| 26. | 5-(benzoyl) (ethoxycarbonyl)methylene-3-(2,4,5,-trichlorophenyl)hydantoin | 250 to 252 |
| 27. | 5-(benzoyl) (ethoxycarbonyl)methylene-3-(p-anisyl)hydantoin | 203 to 205 |
| 28. | 5-(benzoyl) (ethoxycarbonyl)methylene-3-(2-methoxy-4-nitrophenyl)hydantoin | 210 to 212 |
| 29. | 5-(benzoyl) (isopropoxycarbonyl)methylene-3-methylhydantoin | 161 to 162 |
| 30. | 5-(benzoyl) (isopropoxycarbonyl)methylene-3-benzylhydantoin | 189 to 190 |
| 31. | 5-(benzoyl) (isopropoxycarbonyl)- | |

| Nos. | Hydantoin Derivatives | Melting Points (°C.) |
|---|---|---|
| | methylene-3-(3,5-dichlorophenyl)-hydantoin | 237 to 240 |
| 32. | 5-(benzoyl) (isopropoxycarbonyl)-methylene-3-(p-anisyl)hydantoin | 228 to 230 |
| 33. | 5-(acetyl) (ethoxycarbonyl)-methylene-3-ethylhydantoin | 101 to 103 |
| 34. | 5-(acetyl) (ethoxycarbonyl)-methylene-3-phenylhydantoin | 162 |
| 35. | 5-(acetyl) (ethoxycarbonyl)-methylene-3-(p-tolyl)hydantoin | 153 to 155 |
| 36. | 5-(acetyl) (ethoxycarbonyl)-methylene-3-(p-chlorophenyl)-hydantoin | 149 to 150 |
| 37. | 5-(acetyl) (ethoxycarbonyl)-methylene-3-(3,5-dichlorophenyl)-hydantoin | 218 to 220 |
| 38. | 5-(acetyl) (isopropoxycarbonyl)-methylene-3-methylhydantoin | 118 to 120 |
| 39. | 5-(acetyl) (isopropoxycarbonyl)-methylene-3-(n-butyl)hydantoin | 68 to 70 |
| 40. | 5-(acetyl) (isopropoxycarbonyl)-methylene-3-(p-tolyl)hydantoin | 156 to 158 |
| 41. | 5-(acetyl) (isopropoxycarbonyl)-methylene-3-(3,5-dichlorophenyl)-hydantoin | 202 to 204 |
| 42. | 5-(acetyl) (isopropoxycarbonyl)-methylene-3-(p-anisyl)hydantoin | 168 to 170 |
| 43. | 5-(cyano) (ethoxycarbonyl)-methylene-3-isopropylhydantoin | 210 to 211 |
| 44. | 5-(cyano) (ethoxycarbonyl)-methylene-3-allylhydantoin | 168 to 169 |
| 45. | 5-(cyano) (ethoxycarbonyl)-methylene-3-cyclohexylhydantoin | 232 to 233 |
| 46. | 5-(cyano) (ethoxycarbonyl)-methylene-3-phenylhydantoin | 234 to 236 |
| 47. | 5-(cyano) (ethoxycarbonyl)-methylene-3-(p-tolyl)hydantoin | 276 to 278 |
| 48. | 5-(cyano) (ethoxycarbonyl)-methylene-3-(3,5-dichlorophenyl)hydantoin | 285 to 287 |
| 49. | 5-(cyano) (methoxycarbonyl)-methylene-3-isopropylhydantoin | 217 to 218.5 |
| 50. | 5-(cyano) (methoxycarbonyl)-methylene-3-benzylhydantoin | 246 to 248 |
| 51. | 5-(cyano) (methoxycarbonyl)-methylene-3-(3,4-xylyl)hydantoin | 255 to 257 |
| 52. | 5-(cyano) (methoxycarbonyl)-methylene-3-(3,5-dichlorophenyl)-hydantoin | 268 to 269 |
| 53. | 5-(cyano) (methoxycarbony)-methylene-3-(2-methoxy-4-nitrophenyl)hydantoin | 248 to 250 |
| 54. | 5-bis(acetyl)methylene-3-ethylhydantoin | 152 to 153 |
| 55. | 5-bis(acetyl)methylene-3-allylhydantoin | 154 to 156 |
| 56. | 5-bis(acetyl)methylene-3-benzylhydantoin | 211 to 212 |
| 57. | 5-bis(acetyl)methylene-3-phenylhydantoin | 230 to 233 |
| 58. | 5-bis(acetyl)methylene-3-(3,5-dichlorophenyl)hydantoin | 254 to 255 |
| 59. | 5-bis(acetyl)methylene-3-(p-anisyl)hydantoin | 221 to 223 |
| 60. | 5-(benzoyl) (ethoxycarbonyl)-methylenehydantoin | 229 to 231 |

Now, Examples for the preparations of hydantoin derivatives according to the present invention will be given below:

EXAMPLE 1

(Compound No. 1)

To 80 ml of 1,2-dichloroethane containing 4.4 millimoles of tetraethylammonium fluoride and 20.0 millimoles of 1-amino-1,2,2-tris(ethoxycarbonyl)ethylene (melting point: 69.5° to 70° C.), 50.0 millimoles of triethylamine was added at room temperature, and then the 20 ml of 1,2-dichloroethane containing 50.1 millimoles of isopropylisocyanate was dropwise added. The mixture was stirred at room temperature for 20 hours.

The reaction product mixture was concentrated under reduced pressure. After adding 20 ml of ethanol, the residue was filtered, and 4.77 g of crystals of 5-bis(ethoxycarbonyl)methylene-3-isopropyl hydantoin were obtained. The crystals were recrystallized from ethanol, whereupon 2.76 g. of colourless needles having a melting point of from 101° to 103° C. were obtained. The results (unit of the values: % by weight; the same is true hereinafter) obtained by their elemental analysis are shown below:

| | C | H | N |
|---|---|---|---|
| Analytical values | 52.32 | 6.04 | 9.30 |
| Calculated values (as $C_{13}H_8N_2O_5$) | 52.35 | 6.08 | 9.39 |

EXAMPLE 2

(Compound No. 3)

To 25 ml of dichloromethane containing 11.1 millimoles of 1-amino-1,2,2-tris(ethoxycarbonyl)ethylene and 26.7 millimoles of pyridine, 15 ml of dichloromethane containing 13.3 millimoles of phosgene was dropwise added under ice-cooling, and then reacted at room temperature for 2 hours with stirring.

To the reaction product mixture, 10 ml of dichloromethane containing 15.6 millimoles of allylamine was dropwise added under ice-cooling, and then reacted under reflux for 2 hours with stirring.

After adding 100 ml of water, the reaction product mixture was separated, and the organic solvent layer was dried over anhydrous sodium sulfate, and then concentrated under reduced pressure. To the residue, 100 ml of benzene containing 18.7 millimoles of triethylamine was added and reacted under reflux for 3 hours.

The reaction product mixture was concentrated under reduced pressure, and the residual crystals were recrystallized from ethanol, whereupon 0.60 g. of colourless needles (melting point: 91° to 92° C.) of 5-bis(ethoxycarbonyl)methylene-3-allyl hydantoin were obtained. Their elemental analytical values are shown as follows:

| | C | H | N |
|---|---|---|---|
| Analytical values: | 52.49 | 5.45 | 9.29 |
| Calculated values: (as $C_{13}H_{16}N_2O_6$) | 52.70 | 5.44 | 9.46 |

EXAMPLE 3

(Compound No. 4)

Added successively to 80 ml of 1,2-dichloroethane containing 4.2 millimoles of tetraethylammonium fluoride, were 10 ml of 1,2-dichloroethane containing 20.0 millimoles of 1-amino-1,2,2-triethoxycarbonylethylene, 10 ml of 1,2-dichloroethane containing 50 millimoles of cyclohexylisocyanate and 10 ml of 1,2-dichloroethane containing 50.0 millimoles of triethylamine. The mixture was stirred at room temperature for 3 hours.

To the reaction product mixture was added 25 ml of 2 N hydrochloric acid under ice-cooling, and the mixture was filtered. The filtrate was separated, and the organic layer was dried over anhydrous sodium sulfate, and then concentrated under reduced pressure. To the residue, 30 ml of ethanol was added, and then filtered, whereupon 2.87 g. of crystals of 5-bis-(ethoxycarbonyl)-methylene-3-cyclohexyl hydantoin were obtained. The crystals were recrystallized from ethanol, whereupon colourless needles having a melting point of from 118° to 121° C. were obtained. From the elemental analysis, the following results were obtained.

|  | C | H | N |
|---|---|---|---|
| Analytical values: | 56.87 | 6.35 | 8.21 |
| Calculated values: (as $C_{16}H_{22}N_2O_6$) | 56.79 | 6.55 | 8.28 |

EXAMPLE 4

(Compound No. 5)

Added dropwise under ice-cooling to 50 ml of 1,2-dichloroethane containing 20.0 millimoles of 1-amino-1,2,2-tris(ethoxycarbonyl)ethylene and 48.0 millimoles of pyridine, was 20 ml of 1,2-dichloroethane containing 10.8 millimoles of trichloromethyl chloroformate. The mixture was stirred at room temperature for 2 hours.

To the reaction product mixture was dropwise added 30 ml of 1,2-dichloroethane containing 20.0 millimoles of benzylamine under ice-cooling, and the mixture was stirred at room temperature for 20 hours.

To the reaction product mixture, 50 ml of water was added, and the mixture was then separated. The organic layer thereby obtained was dried over anhydrous sodium sulfate, and then concentrated under reduced pressure. To the residue, 100 ml of benzene containing 20.0 millimoles of triethylamine was added, and the mixture was refluxed for 1.5 hours.

The reaction product mixture thereby obtained, was concentrated under reduced pressure, and the residual crystals were recrystallized from ethanol, whereby 2.15 g. of colourless needles (melting point: 149° to 151° C.) of 5-bis(ethoxycarbonyl)methylene-3-benzylhydantoin were obtained. The results of the elemental analysis thereof are as follows:

|  | C | H | N |
|---|---|---|---|
| Analytical values: | 58.85 | 5.15 | 7.92 |
| Calculated values: (as $C_{17}H_{18}N_2O_6$) | 58.95 | 5.24 | 8.09 |

EXAMPLE 5

(Compound No. 6)

Added dropwise under ice-cooling to 40 ml of benzene containing 11.0 millimoles of 1-amino-1,2,2-tris-(ethoxycarbonyl)ethylene and 26.3 millimoles of pyridine, was 10 ml of benzene containing 13.2 millimoles of phosgene. The mixture was stirred at room temperature for 2 hours.

To the reaction product mixture, 10 ml of benzene containing 15.4 millimoles of aniline was dropwise added under ice-cooling, and the mixture was refluxed for 30 minutes.

To the reaction product mixture, 30 ml of water was added, and the mixture was filtered. The filtrate was separated, and the organic layer was dried over anhydrous sodium sulfate and concentrated under reduced pressure. To the residual crystals, 30 ml of diisopropyl ether was added, and the mixture was filtered, whereupon 2.33 g. of 5-bis(ethoxycarbonyl)-methylene-3-phenylhydantoin was obtained. The product was recrystallized from benzene, whereupon colourless needles having a melting point of 167.5° C. were obtained. The results of the elemental analysis thereof are as follows:

|  | C | H | N |
|---|---|---|---|
| Analytical values: | 57.94 | 4.85 | 8.23 |
| Calculated values: (as $C_{16}H_{16}N_2O_6$) | 57.83 | 4.85 | 8.43 |

EXAMPLE 6

(Compound No. 8)

Successively added to 50 ml of benzene containing 10.0 millimoles of 1-amino-1,2,2-tris(ethoxycarbonyl)-ethylene, were 0.10 g. of a mineral oil containing 2.1 millimoles of sodium hydride and 50 ml of benzene containing 20.0 millimoles of p-chlorophenylisocyanate. The mixture was refluxed for 7 hours.

To the reaction product mixture, 3 ml of 1 N hydrochloric acid and 17 ml of water were added under ice-cooling, and the mixture was then separated.

The organic layer thereby obtained was dried over anhydrous sodium sulfate, and concentrated under reduced pressure. To the residue, 20 ml of diisopropyl ether was added, and the mixture was filtered, whereupon 3.59 g. of crystals of 5-bis(ethoxycarbonyl)-methylene-3-(p-chlorophenyl)hydantoin were obtained. The crystals were recrystallized from ethanol, whereupon crystals having a melting point of from 161.5° to 162° C. were obtained. The results of the elemental analysis thereof are as follows:

|  | C | H | N | Cl |
|---|---|---|---|---|
| Analytical values: | 52.28 | 4.15 | 7.55 | 9.82 |
| Calculated values: (as $C_{16}H_{15}ClN_2O_6$) | 52.40 | 4.12 | 7.64 | 9.67 |

EXAMPLE 7

(Compound No. 12)

Added dropwise under ice-cooling to 35 ml of benzene containing 13.0 millimoles of 1-amino-1,2,2-tris(ethoxycarbonyl)ethylene and 31.1 millimoles of pyridine, was 15 ml of benzene containing 15.6 millimoles of phosgene. The mixture was stirred at room temperature for 2 hours.

To the reaction product mixture, 18.1 millimoles of 4-nitro-o-anisidine was added under ice-cooling, and the mixture was stirred at room temperature for 10 hours.

To the reaction product mixture thereby obtained, 150 ml of water was added and the mixture was filtered. The filtrate was separated, and the organic layer thereby obtained was dried over anhydrous sodium sulfate and concentrated under reduced pressure. To the residual crystals, 50 ml of ethanol was added, and filtered. The filtered crystals were recrystallized from ethanol, whereupon 0.68 g. of crystals (melting point: 170° to 172° C.) of 5-bis(ethoxycarbonyl)methylene-3-(2-methoxy-4-nitrophenyl) hydantoin were obtained.

The results of the elemental analysis thereof are as follows:

|  | C | H | N |
| --- | --- | --- | --- |
| Analytical values: | 50.06 | 4.44 | 10.09 |
| Calculated values: (as $C_{17}H_{17}N_3O_9$) | 50.13 | 4.21 | 10.32 |

EXAMPLE 8

(Compound No. 16)

Added dropwise under ice-cooling to 50 ml of 1,2-dichloroethane containing 28.5 millimoles of 1-amino-2,2-bis(dimethoxycarbonyl)-1-(ethoxycarbonyl)ethylene (melting point: 72° to 73° C.) and 68.4 millimoles of pyridine, was 20 ml of 1,2-dichloroethane containing 15.3 millimoles of trichloromethyl chloroformate. The mixture was reacted at room temperature for 2 hours under stirring.

To the reaction product mixture, 30 ml of 1,2-dichloroethane containing 28.5 millimoles of p-anisidine was dropwise added under ice-cooling. The mixture was stirred at room temperature for 20 hours.

To the reaction product mixture, 50 ml of water was added, and the mixture was separated. The organic layer thereby obtained was dried over anhydrous sodium sulfate and then concentrated. To the residue, 20 ml of methanol was added, and filtered, whereupon 2.55 g. of crystals of 5-bis(methoxycarbonyl)methylene-3-(p-anisyl) hydantoin were obtained. The crystals were recrystallized from ethyl acetate, whereupon 1.35 g. of yellowish needles having a melting point of from 204° to 206° C. were obtained. The results of the elemental analysis thereof are as follows:

|  | C | H | N |
| --- | --- | --- | --- |
| Analytical values: | 53.61 | 4.21 | 8.28 |
| Calculated values: (as $C_{15}H_{14}N_2O_7$) | 53.90 | 4.22 | 8.38 |

EXAMPLE 9

(Compound No. 18)

To 70 ml of 1,2-dichloroethane containing 5.9 millimoles of tetraethylammonium fluoride, 29.8 millimoles of 1-amino-2-benzoyl-1,2-bis(ethoxycarbonyl)ethylene (melting point: 138° to 139° C.) was added and then 30 ml of 1,2-dichloroethane containing 59.5 millimoles of n-butyl isocyanate was dropwise added. The mixture was stirred at room temperature for 41 hours.

The reaction product mixture was washed with 50 ml of water and separated. The organic layer thereby obtained was dried over anhydrous sodium sulfate, and concentrated under reduced pressure. To the residue, 50 ml of diisopropyl ether was added, and filtered, whereupon 8.25 g. of crystals of 5-(benzoyl) (ethoxycarbonyl)methylene-3-(n-butyl)hydantoin were obtained. The crystals were recrystallized from ethanol, whereupon yellowish needles having a melting point of from 142° to 144° C. were obtained. The results of the elemental analysis thereof are as follows:

|  | C | H | N |
| --- | --- | --- | --- |
| Analytical values: | 62.86 | 5.72 | 7.96 |
| Calculated values: (as $C_{18}H_{20}N_2O_5$) | 62.78 | 5.85 | 8.14 |

EXAMPLE 10

(Compound No. 19)

Added dropwise under ice-cooling to 60 ml of dichloromethane containing 29.6 millimoles of 1-amino-2-benzoyl-1,2-bis(ethoxycarbonyl)ethylene and 70.9 millimoles of pyridine, was 30 ml of dichloromethane containing 35.5 millimoles of phosgene. The mixture was stirred for 2 hours at room temperature.

To the reaction product mixture, 20 ml of dichloromethane containing 41.3 millimoles of allylamine was dropwise added under ice-cooling, and the mixture was stirred at room temperature for 10 hours.

To the reaction product mixture, 50 ml of water was added, and the mixture was separated. The organic layer thus obtained was concentrated under reduced pressure.

To the residue, 29.8 millimoles of triethylamine and 50 ml of benzene was added, and the mixture was refluxed for one hour.

The reaction product mixture was cooled and filtered, whereupon 3.69 g. of crystals of 5-(benzoyl) (ethoxycarbonyl)methylene-3-allylhydantoin were obtained. These crystals were recrystallized from benzene, whereupon 3.07 g. of yellowish needles having a melting point of from 176° to 178° C. were obtained. The results of the elemental analysis thereof are as follows:

|  | C | H | N |
| --- | --- | --- | --- |
| Analytical values: | 62.09 | 4.91 | 8.47 |
| Calculated values: (as $C_{17}H_{16}N_2O_5$) | 62.19 | 4.91 | 8.53 |

EXAMPLE 11

(Compound No. 20)

To 80 ml of 1,2-dichloroethane containing 4.3 millimoles of tetraethylammonium fluoride, 20.0 millimoles of 1-amino-2-benzoyl-1,2-bis(ethoxycarbonyl)ethylene was added, and then 20 ml of 1,2-dichloroethane containing 45.0 millimoles of cyclohexyl isocyanate was dropwise added. The mixture was refluxed for 5 hours.

The reaction product mixture was concentrated under reduced pressure. To the residue, 50 ml of diisopropyl ether was added, and filtered, whereupon 6.90 g. of crystals of 5-(benzoyl) (ethoxycarbonyl)methylene-3-cyclohexylhydantoin were obtained. The crystals were recrystallized from ethanol, whereupon colourless needles having a melting point of from 184° to 186° C. were obtained. The results of the elemental analysis thereof are as follows:

|  | C | H | N |
| --- | --- | --- | --- |
| Analytical values: | 64.85 | 6.03 | 7.52 |
| Calculated values: (as $C_{20}H_{22}N_2O_5$) | 64.85 | 5.99 | 7.56 |

EXAMPLE 12

(Compound No. 22)

To 30 ml of benzene containing 10.0 millimoles of 1-amino-2-benzoyl-1,2-bis(ethoxycarbonyl)methylene, 10 ml of benzene containing 20.0 millimoles of triethylamine was added at room temperature, and then 15 ml of benzene containing 25.0 millimoles of p-tolyl isocyanate was dropwise added. The mixture was stirred at room temperature for 20 hours.

The reaction product mixture was filtered, and the filtrate was concentrated under reduced pressure. To the residue, 30 ml of diisopropyl ether was added, and filtered, whereupon 2.74 g. of crystals of 5-(benzoyl)(ethoxycarbonyl)methylene-3-(p-tolyl)-hydantoin were obtained. The crystals were recrystallized from ethanol, whereupon 2.07 g. of yellowish needles having a melting point of from 205° to 206° C. were obtained. The results of the elemental analysis thereof are as follows:

|  | C | H | N |
| --- | --- | --- | --- |
| Analytical values: | 66.80 | 4.87 | 7.41 |
| Calculated values: (as $C_{21}H_{18}N_2O_5$) | 66.66 | 4.79 | 7.40 |

EXAMPLE 13

(Compound No. 26)

Added dropwise under ice-cooling to 70 ml of dichloromethane containing 43.3 millimoles of 1-amino-2-benzoyl-1,2-bis(ethoxycarbonyl)ethylene and 103.9 millimoles of pyridine, was 30 ml of dichloromethane containing 52.0 millimoles of phosgene. The mixture was stirred at room temperature for 2 hours.

To the reaction product mixture, 50 ml of dichloromethane containing 60.6 millimoles of 2,4,5-trichloroaniline was dropwise added. The mixture was stirred at room temperature for 10 hours.

The reaction product mixture was treated in the same manner as in Example 7 except that benzene was used as the solvent for recrystallization, whereupon 6.25 g. of colourless crystals (melting point: 250° to 252° C.) of 5-(benzoyl)(ethoxycarbonyl)methylene-3-(2,4,5-trichlorophenyl)hydantoin were obtained. The results of the elemental analysis thereof are as follows:

|  | C | H | N | Cl |
| --- | --- | --- | --- | --- |
| Analytical values: | 51.47 | 2.89 | 5.94 | 22.97 |
| Calculated values: (as $C_{20}H_{13}Cl_3N_2O_5$) | 51.36 | 2.80 | 5.99 | 22.74 |

EXAMPLE 14

(Compound No. 33)

To 80 ml of 1,2-dichloroethane containing 12.6 millimoles of tetraethylammonium fluoride, 58.9 millimoles of 1-acetyl-2-amino-1,2-bis(ethoxycarbonyl)ethylene (melting point: 88° to 89° C.) was added and then 20 ml of 1,2-dichloroethane containing 117.8 millimoles of ethyl isocyanate was dropwise added. The mixture was refluxed for 5 hours.

The reaction product mixture was treated in the same manner as in Example 9 except that diisopropyl ether was used as the solvent for recrystallization, whereupon yellowish crystals (melting point: 101° to 103° C.) of 5-(acetyl)(ethoxycarbonyl)methylene-3-ethyl hydantoin were obtained. The results of the elemental analysis thereof are as follows:

|  | C | H | N |
| --- | --- | --- | --- |
| Analytical values: | 51.99 | 5.52 | 11.15 |
| Calculated values: (as $C_{11}H_{14}N_2O_6$) | 51.97 | 5.55 | 11.02 |

EXAMPLE 15

(Compound No. 34)

To benzene containing 10.0 millimoles of 1-acetyl-2-amino-1,2-bis(ethoxycarbonyl)ethylene, 10 ml of benzene contaning 20.0 millimoles of triethylamine was added at room temperature, and then 150 ml of benzene containing 25.0 millimoles of phenyl isocyanate was dropwise added. The mixture was stirred at room temperature for 20 hours.

The reaction product mixture was treated in the same manner as in Example 12, whereupon 1.60 g. of yellowish needles (melting point: 162° C.) of 5-(acetyl)(ethoxycarbonyl)methylene-3-phenyl hydantoin were obtained. The results of the elemental analysis thereof are as follows:

|  | C | H | N |
| --- | --- | --- | --- |
| Analytical values: | 59.68 | 4.68 | 9.28 |
| Calculated values: (as $C_{15}H_{14}N_2O_5$) | 59.60 | 4.67 | 9.27 |

EXAMPLE 16

(Compound No. 43)

To 30 ml of 1,2-dichloroethane containing 1.5 millimoles of tetraethylammonium fluoride, 5.0 millimoles of 1-amino-2-cyano-1,2-bis(ethoxycarbonyl)ethylene (melting point: 76° to 77° C.) was added and then 10 ml of 1,2-dichloroethane containing 12.5 millimoles of isopropyl isocyanate was dropwise added. The mixture was refluxed for 6 hours.

The reaction product mixture was treated in the same manner as in Example 9, whereupon 0.69 g. of colourless needles (melting point: 210° to 211° C.) of 5-(cyano)(ethoxycarbonyl)methylene-3-isopropyl hydantoin were obtained. The results of the elemental analysis thereof are as follows:

|  | C | H | N |
| --- | --- | --- | --- |
| Analytical values: | 52.49 | 5.22 | 16.71 |
| Calculated values: (as $C_{11}H_{13}N_3O_4$) | 52.59 | 5.22 | 16.72 |

EXAMPLE 16

(Compound No. 44)

Added dropwise under ice-cooling to 60 ml of dichloromethane containing 30.0 millimoles of 1-amino-2-cyano-1,2-bis(ethoxycarbonyl)ethylene, and 72.1 millimoles of pyridine, was 10 ml of dichloromethane containing 35.7 millimoles of phosgene. The mixture was stirred at room temperature for 5 hours.

To the reaction product mixture, 30 ml of dichloromethane containing 30.1 millimoles of allylamine was dropwise added under ice-cooling. The mixture was stirred at room temperature for 10 hours.

The reaction product mixture was treated in the same manner as in Example 9, whereupon 2.62 g. of colourless needles (melting point: 168° to 169° C.) of 5-(cyano)(ethoxycarbonyl)methylene-3-allyl hydantoin were obtained. The results of the elemental analysis thereof are as follows:

|  | C | H | N |
|---|---|---|---|
| Analytical values: | 53.64 | 4.29 | 17.18 |
| Calculated values: (as $C_{11}H_{11}N_3O_4$) | 53.01 | 4.45 | 16.86 |

EXAMPLE 17

(Compound No. 45)

To 30 ml of 1,2-dichloroethane containing 1.0 millimole of tetraethylammonium fluoride and 5.0 millimoles of 1-amino-2-cyano-1,2-bis(ethoxycarbonyl)ethylene, 10 ml of 1,2-dichloroethane containing 12.2 millimoles of cyclohexyl isocyanate was dropwise added at room temperature and then 12.5 millimoles of triethylamine was added. The mixture was stirred at room temperature for 5 hours.

The reaction product mixture was concentrated under reduced presusre, and to the residue, 30 ml of ethanol was added, and filtered, whereupon 1.65 g. of crystals of 5-(cyano)(ethoxycarbonyl)methylene-3-cyclohexyl hydantoin were obtained. These crystals were recrystallized from ethanol, whereby 0.69 g of colourless needles having a melting point of from 232° to 233° C. were obtained. The results of the elemental analysis thereof are as follows:

|  | C | H | N |
|---|---|---|---|
| Analytical values: | 57.93 | 5.95 | 14.50 |
| Calculated values: (as $C_{14}H_{17}N_3O_4$) | 57.72 | 5.88 | 14.42 |

EXAMPLE 18

(Compound No. 46)

To 30 ml of benzene containing 5.0 millimoles of 1-amino-2-cyano-1,2-bis(ethoxycarbonyl)methylene, 15 ml of benzene containing 10.0 millimoles of triethylamine was dropwise added at room temperature, and then 15 ml of benzene containing 14.2 millimoles of phenyl isocyanate was dropwise added. The mixture was stirred at room temperature for 20 hours.

To the reaction product mixture 14.5 ml of 1 N hydrochloric acid and 15.5 ml of water were added under ice-cooling, and then filtered, whereupon 1.44 g. of 5-(cyano)(ethoxycarbonyl)methylene-3-phenyl hydantoin was obtained. The product was recrystallized from ethaol, whereupon 1.10 g. of yellowish needles having a melting point of from 234° to 236° C. were obtained. The results of the elemental analysis thereof are as follows:

|  | C | H | N |
|---|---|---|---|
| Analytical values: | 59.16 | 4.02 | 14.63 |
| Calculated values: (as $C_{14}H_{11}N_3O_4$) | 58.95 | 3.89 | 14.73 |

EXAMPLE 19

(Compound No. 50)

To 40 ml of 1,2-dichloroethane containing 1.1 millimoles of tetraethylammonium fluoride and 5.5 millimoles of 1-amino-2-cyano-1-ethoxycarbonyl-2-(methoxycarbonyl)ethylene (melting point: 115° to 116° C.), 20 ml of 1,2-dichloroethane containing 22.5 millimoles of benzyl isocyanate was dropwise added at room temperature, and then 11.4 millimoles of triethylamine was added. The mixture was stirred at room temperature for 2.5 hours.

The reaction product mixture was washed with 50 ml of water, dried over anhydrous sodium sulfate, and then concentrated under reduced pressure. To the residue, 50 ml of isopropyl alcohol was added, and then filtered, whereupon 1.14 g. of crystals of 5-(cyano)(methoxycarbonyl)methylene-3-benzyl hydantoin were obtained. The crystals were recrystallized from acetonitrile, whereupon 0.53 g. of colourless needles having a metling point of from 246° to 248° C. were obtained. The results of the elemental analysis thereof are as follows:

|  | C | H | N |
|---|---|---|---|
| Analytical values: | 59.00 | 3.96 | 14.77 |
| Calculated values: (as $C_{14}H_{11}N_3O_4$) | 58.95 | 3.89 | 14.73 |

EXAMPLE 20

(Compound No. 53)

Added dropwise under ice-cooling to 30 ml of 1,2-dichloroethane containing 10.1 millimoles of 1-amino-2-cyano-1-ethoxycarbonyl-2-(methoxycarbonyl)ethylene and 24.3 millimoles of pyridine, was 20 ml of 1,2-dichloroethane containing 5.4 millimoles of trichloromethyl chloroformate. The mixture was stirred at room temperature for 2 hours.

To the reaction product mixture, 50 ml of 1,2-dichloroethane containing 10.1 millimoles of 2-methoxy-4-nitroaniline was added. The mixture was stirred at room temperature for 24 hours.

To the reaction product mixture, 50 ml of water was added and then filtered, whereupon 1.20 g of cyrstals of 5-(cyano)(methoxycarbonyl)methylene-3-(2-methoxy-4-nitrophenyl)hydantoin were obtained.

The filtrate was separated, and the organic layer was dried over anhydrous sodium sulfate and then concentrated. The residue was recrystallized from methanol, whereupon 0.29 g. of yellowish needles (melting point: 248° to 250° C.) of 5-(cyano)(methoxycarbonyl)methylene-3-(2-methoxy-4-nitrophenyl)hydantoin were obtained. The results of the elemental analysis thereof are as follows:

|  | C | H | N |
|---|---|---|---|
| Analytical values: | 48.37 | 3.03 | 15.88 |
| Calculated values: (as $C_{14}H_{10}N_4O_7$) | 48.56 | 2.91 | 16.18 |

EXAMPLE 21

(Compound No. 54)

To 95 ml of 1,2-dichloroethane containing 3.0 millimoles of tetraethylammonium fluoride, 30.0 millimoles of 1-amino-2,2-diacetyl-1-(ethoxycarbonyl)ethylene (melting point: 75° to 76° C.) was added and then 25 ml of 1,2-dichloroethane containing 60.1 millimoles of ethyl isocyanate was dropwise added. The mixture was refluxed for 12.5 hours.

The reaction product mixture was treated in the same manner as in Example 9, whereupon 2.43 g. of yellowish needles (melting point: 152° to 153° C.) of 5-bis-(acetyl)methylene-3-ethyl hydantoin were obtained. The results of the elemental analysis thereof are as follows:

|  | C | H | N |
|---|---|---|---|
| Analytical values: | 53.46 | 5.42 | 12.47 |
| Calculated values: (as $C_{10}H_{12}N_2O_4$) | 53.57 | 5.39 | 12.49 |

EXAMPLE 22

(Compound No. 55)

To 35 ml of 1,2-dichloroethane containing 2.4 millimoles of tetraethylammonium fluoride and 10.0 millimoles of 1amino-2,2-diacetyl-1-(ethoxycarbonyl)ethylene, 10 ml of 1,2-dichloroethane containing 27.9 millimoles of allyl isocyanate was added at a room temperature and then 10 ml of 1,2-dichloroethane containing 20.0 millimoles of triethylamine was dropwise added. The mixture was stirred at room temperature for 20 hours.

The reaction product mixture was concentrated under reduced pressure. To the residue, 30 ml of ethanol was added, and then filtered, whereupon 1.31 g. of crystals of 5-bis(acetyl)methylene-3-allyl hydantoin were obtained. These crystals were recrystallized from ethanol, whereupon 0.82 g. of yellowish needles having a melting point of from 154° to 156° C. were obtained. The results of the elemental analysis thereof are as follows:

|  | C | H | N |
|---|---|---|---|
| Analytical values: | 56.19 | 5.08 | 12.00 |
| Calculated values: (as $C_{11}H_{12}N_2O_4$) | 55.93 | 5.12 | 11.86 |

EXAMPLE 23

(Compound No. 56)

To 50 ml of 1,2-dichloroethane containing 2.7 millimoles of tetraethylammonium fluoride, 13.2 millimoles of 1-amino-2,2-diacetyl-1-(ethoxycarbonyl)ethylene was added, and then 25 ml of 1,2-dichloroethane containing 26.3 millimoles of benzyl isocyanate was dropwise added. The mixture was refluxed for 3 hours.

To the reaction product mixture, 25 ml of water was added, and filtered, whereupon 1.00 g. of crystals of 5-bis(acetyl)methylene-3-benzyl hydantoin were obtained. The filtrate was separated, and the organic layer was concentrated under reduced pressure. The residue thereby obtained was recrystallized from ethanol, whereupon 1.54 g. of yellowish needles (melting point: 211° to 212° C.) of 5-bis(acetyl)methylene-3-benzyl hydantoin were obtained. The results of the elemental analysis thereof are as follows:

|  | C | H | N |
|---|---|---|---|
| Analytical values: | 62.67 | 4.91 | 9.73 |
| Calculated values: (as $C_{15}H_{14}N_2O_4$) | 62.93 | 4.93 | 9.80 |

EXAMPLE 24

(Compound No. 57)

To 40 ml of benzene containing 10.0 millimoles of 1-amino-2,2-diacetyl-1-(ethoxycarbonyl)ethylene, 10 ml of benzene containing 20.0 millimoles of triethylamine and then 10 ml of benzene containing 20.0 millimoles of phenyl isocyanate were dropwise added at room temperature. The mixture was stirred at room temperature for 20 hours.

To the reaction product mixture, 20 ml of 1 N hydrochloric acid and 10 ml of water were added, and filtered, whereupon 2.54 g. of 5-bis(acetyl)methylene-3-phenyl hydantoin was obtained. The product was recrystallized from benzene, whereupon 1.75 g. of yellowish needles having a melting point of from 230° to 233° C. were obtained. The results of the elemental analysis thereof are as follows:

|  | C | H | N |
|---|---|---|---|
| Analytical values: | 62.04 | 4.55 | 10.30 |
| Calculated values: (as $C_{14}H_{12}N_2O_4$) | 61.76 | 4.44 | 10.29 |

EXAMPLE 25

(Compound No. 59)

To 15 ml of benzene containing 5.0 millimoles of 1-amino-2,2-diacetyl-1-(ethoxycarbonyl)ethylene, 5 ml of benzene containing 10.0 millimoles of triethylamine and then 10 ml of benzene containing 12.5 millimoles of p-anisyl isocyanate were dropwise added at room temperature. The mixture was stirred at room temperature for 24 hours.

The reaction product mixture was filtered, whereupon 1.52 g. of crystals of 5-bis(acetyl)methylene-3-(p-anisyl)hydantoin were obtained. The crystals were recrystallized from ethanol, whereupon 0.84 g. of yellowish needles having a melting point of from 221° to 223° C. were obtained. The results of the elemental analysis thereof are as follows:

|  | C | H | N |
|---|---|---|---|
| Analytical values: | 59.55 | 4.86 | 9.29 |
| Calculated values: (as $C_{15}H_{14}N_2O_5$) | 59.60 | 4.67 | 9.27 |

EXAMPLE 26

(Compound No. 60)

Added dropwise under ice-cooling to 120 ml of chlorobenzene containing 14.9 millimoles of 1-amino-2-benzoyl-1,2-bis(ethoxycarbonyl)methylene and 32.7 millimoles of pyridine, was 30 ml of chlorobenzene containing 16.4 millimoles of phosgene. The mixture was stirred for 2 hours.

To the reaction product mixture, 5.96 g. of an aqueous 28 wt.% ammonium solution was dropwise added, and the mixture was stirred for 3 hours.

To the reaction product mixture, 50 ml of water was added and then filtered, whereupon 0.74 g. of crystals of 5-(benzoyl) (ethoxycarbonyl)methylene hydantoin were obtained. The crystals were recrystallized from ethanol, whereupon 0.43 g. of colourless needles having a melting point of from 229° to 231° C. were obtained. The results of the elemental analysis thereof are as follows:

|  | C | H | N |
|---|---|---|---|
| Analytical values: | 58.40 | 4.28 | 9.65 |
| Calculated values: (as $C_{14}H_{12}N_2O_5$) | 58.33 | 4.20 | 9.72 |

Now, Test Examples will be given which establish usefulness of the compounds of the present invention as germicides for agricultural and horticultural purposes. In the Test Examples, "parts" means "parts by weight".

Test Example 1

Test for controlling powdery mildew (1) Preparation of Test Emulsions

Twenty parts of a test sample, 5 parts of TOXANON and 75 parts of xylene were mixed to obtain 100 parts of an emulsion.

(2) Controlling Test

A cucumber (variety: Sagami Hannichi-Sessei) was cultivated in a synthetic resin pot having a diameter of 6 cm (one plant per pot). To a young seedling of 17 days old after the seeding of the cucumber seed, the emulsion prepared according to the above method was applied (the test sample concentration: 1,000 ppm). After air-drying, the yound seedling was inoculated with a suspension of powdery mildew bacteria (Sphaerotheca fuliginea) (i.e. a spore suspension prepared by suspending in distilled water, conidiospores collected into a Petri dish with use of a soft brush, from the leaf surface of a leaf diseased with powdery mildew, in such a concentration that 10 conidiospores were observed in one field of view of an optical microscope (magnification: 150 times)) by uniform spraying. The inoculated young seedling was left in an isolated glass hot-house(greenhouse). On about the 11th day thereafter, the number of lesions of powdery mildew which appeared on the first foliage leaf, was counted, and the controlling rate of each test sample was calculated according to the following calculation method, and the controlling grade was determined according to the standard which is given below. The results thereby obtained are shown in Table 1.

$$\text{Controlling rate (\%)} = \left(1 - \frac{\text{the average number of lesions in the treated area}}{\text{the average number of lesions in the untreated area}}\right) \times 100$$

| Controlling Grades | Controlling rates (%) |
|---|---|
| 5 | 91 to 100 |
| 4 | 81 to 90 |
| 3 | 61 to 80 |

TABLE 1

| Test Samples | Controlling Grades | Phytotoxicity |
|---|---|---|
| Compound No. 2 | 4 | None |
| Compound No. 9 | 4 | None |
| Compound No. 12 | 3 | None |
| Compound No. 39 | 4 | None |
| Compound No. 44 | 3 | None |
| Compound No. 46 | 3 | None |
| Morestan* | 5 | None |

*Control sample

Test Example 2

Test for controlling bacterial leaf blight (submerged application)

(1) Preparation of Wettable Test Samples

Twenty parts of a test sample, one part of DEMOL, 20 parts of white carbon and 59 parts of talc were mixed and pulverized to obtain 100 parts of a wettable sample.

(2) Controlling Test

Paddy-field rice seeds (variety: Nihonbare) were seeded in a synthetic resin pot having a diameter of 6 cm (5 seeds per pot), and cultivated in a glass hot-house. Rice plants of from 5.5 to 6.5 leaf stage were subjected to the test. The wettable sample prepared according to the above mentioned method was diluted with water to have a concentration of the test sample being 500 ppm, and 3 ml of the diluted sample was applied in a submerged application manner. After the application, the pot was left for 2 days in the glass hot-house to permit the sample to be adequately absorbed from the root, and then the inoculation was conducted. The inoculum was prepared by culturing bacterial leaf blight bacteria (Xanthomonas oryzeae) in a SUWA liquid culture medium at 28° C. for 48 hours by shake culture and by adjusting the concentration so that there were $10^{7-8}$ bacteria per ml. The inoculation was made into the leaf blades of the upper two leaves by a double needle inoculation avoiding the inoculation to the mid-vein. After the inoculation, the plants were kept in the glass hot-house. Two weeks after the inoculation, the number of rice plants ($n_1$ to $n_7$) diseased with bacterial leaf blight was counted for the respective degrees of disease according to the following evaluation standard. The number of test plants was 30 plants in each area.

Evaluation Standards for the Diseased Degrees

0: No disease was observed (number of rice plants: n)

1: Slight disease was observed (number of rice plants: $n_2$)

2: A lesion of not greater than 1 cm was obersed (number of rice plants: $n_3$)

3: A lesion of not greater than 2 cm was observed (number of rice plants: $n_4$)

4: A lesion of not greater than 5 cm was observed (number of rice plants: $n_5$)
5: A lesion of not greater than 10 cm was observed (number of rice plants: $n_6$)
6: A lesion of greater than 10 cm was observed (number of rice plants: $n_7$)

On the basis of the above evaluation, the controlling rate of each test sample was calculated according to the equation given below, and then the controlling grade was determined.

Controlling rate (%) =

$$\left\{1 - \frac{\text{treated area } (0 \times n_1 + 1 \times n_2 + 2 \times n_3 + 3 \times n_4 + 4 \times n_5 + 5 \times n_6 + 6 \times n_7)}{\text{untreated area } (0 \times n_1 + 1 \times n_2 + 2 \times n_3 + 3 \times n_4 + 4 \times n_5 + 5 \times n_6 + 6 \times n_7)}\right\} \times 100$$

The results thereby obtained are shown in Table 2.

TABLE 2

| Test Samples | Controlling Grades | Phytotoxicity |
| --- | --- | --- |
| Compound No. 15 | 3 | None |
| Compound No. 23 | 4 | None |
| Compound No. 25 | 4 | None |
| Compound No. 29 | 3 | None |
| Compound No. 30 | 3 | None |
| Compound No. 32 | 3 | None |
| Compound No. 41 | 4 | None |
| Compound No. 49 | 3 | None |
| Compound No. 51 | 4 | None |
| Compound No. 54 | 4 | None |
| Compound No. 56 | 3 | None |
| Compound No. 58 | 4 | None |
| Phenazine* | 4 | None |

*Control sample

Test Example 2

Test for controlling vacterial leaf blight (foliage application)

Paddy-field rice seeds (variety: Nihonbare) were seeded in a synthetic resin pot having a diameter of 6 cm (5 seeds per pot), and cultivated in a glass hot-house. Rice plants of from 5.5 to 6.5 leaf stage were subjected to the test. The inoculation was made into the leaf blades of the upper two leaves of each rice plant by a double needle inoculation avoiding the inoculation to the mid-vein. The inoculum was the same as used in Test Example 2. After the inoculation, the wettable sample prepared in Test Example 2 (the test sample concentration of 500 ppm) was applied in a foliage application manner. After the application, the plants were kept in the glass hot-house. Two weeks after the inoculation, the controlling rate of each test sample was calculated in the same manner as in Test Example 2, and then the controlling grade was determined. The results thereby obtained are shown in Table 3. The number of the sample plants was 30 plants in each area.

TABLE 3

| Test Samples | Controlling Grades | Phytotoxicity |
| --- | --- | --- |
| Compound No. 14 | 4 | None |
| Compound No. 15 | 4 | None |
| Compound No. 19 | 3 | None |
| Compound No. 20 | 4 | None |
| Compound No. 23 | 4 | None |
| Compound No. 29 | 4 | None |
| Compound No. 30 | 4 | None |
| Compound No. 32 | 3 | None |
| Compound No. 37 | 4 | None |

TABLE 3-continued

| Test Samples | Controlling Grades | Phytotoxicity |
| --- | --- | --- |
| Compound No. 45 | 3 | None |
| Compound No. 49 | 4 | None |
| Compound No. 51 | 4 | None |
| Phenazine* | 5 | None |

*Control sample

What is claimed is:

1. A hydantoin derivative represented by the formula $$\begin{array}{c} H \\ O=C-N \\ | \quad\quad\quad C=C \\ R^1-N-C \\ \| \\ O \end{array} \begin{array}{c} X^1 \\ Y \end{array}$$

where, $R^1$ represents a hydrogen atom, an alkyl group of from 1 to 4 carbon atoms, an allyl group, a cyclohexyl group, a benzyl group or a group

[benzene ring with substituent $R_n^2$]

(where $R^2$ represents an alkyl group of from 1 to 4 carbon atoms, an alkoxy group of from 1 to 4 carbon atoms, a halogen atom or a nitro group, and n is 0, 1, 2 or 3), $X^1$ represents an alkoxycarbonyl group of from 2 to 5 carbon atoms, a benzoyl group, an aliphatic acyl group of from 2 to 5 carbon atoms or a cyano group, and Y represents an alkoxycarbonyl group of from 2 to 5 carbon atoms or an aliphatic acyl group of from 2 to 5 carbon atoms.

2. The hydantoin derivative as claimed in claim 1, which is selected from the group consisting of:
5-bis(ethoxycarbonyl)methylene-3-isopropylhydantoin
5-bis(ethoxycarbonyl)methylene-3-(n-butyl)hydantoin
5-bis(ethoxycarbonyl)methylene-3-allylhydantoin
5-bis(ethoxycarbonyl)methylene-3-cyclohexylhydantoin
5-bis(ethoxycarbonyl)methylene-3-benzylhydantoin
5-bis(ethoxycarbonyl)methylene-3-phenylhydantoin
5-bis(ethoxycarbonyl)methylene-3-(p-tolyl)hydantoin
5-bis(ethoxycarbonyl)methylene-3-(p-chlorophenyl)hydantoin
5-bis(ethoxycarbonyl)methylene-3-(2,5-dichlorophenyl)hydantoin
5-bis(ethoxycarbonyl)methylene-3(3,5-dichlorophenyl)hydantoin
5-bis(ethoxycarbonyl)methylene-3-(2,4,5-trichlorophenyl)hydantoin
5-bis(ethoxycarbonyl)methylene-3-(2-methoxy-4-nitrophenyl)hydantoin
5-bis(methoxycarbonyl)methylene-3-isopropylhydantoin
5-bis(methoxycarbonyl)methylene-3-benzylhydantoin
5-bis(methoxycarbonyl)methylene-3-(3,5-dichlorophenyl)hydantoin
5-bis(methoxycarbonyl)methylene-3-(p-anisyl)hydantoin
5-(benzoyl) (ethoxycarbonyl)methylene-3-isopropylhydantoin 5-(benzoyl) (ethoxycarbonyl)methylene-3-(n-butyl)hydantoin
5-(benzoyl) (ethoxycarbonyl)methylene-3-allylhydantoin
5-(benzoyl) (ethoxycarbonyl)methylene-3-cyclohexylhydantoin
5-(benzoyl) (ethoxycarbonyl)methylene-3-phenylhydantoin
5-(benzoyl) (ethoxycarbonyl)methylene-3-(p-tolyl)hydantoin
5-(benzoyl) (ethoxycarbonyl)methylene-3-(3,4-xylyl)hydantoin
5-(benzoyl) (ethoxycarbonyl)methylene-3-(2,5-dichlorophenyl)hydantoin
5-(benzoyl) (ethoxycarbonyl)methylene-3-(3,5-dichlorophenyl)hydantoin
5-benzoyl) (ethoxycarbonyl)methylene-3-(2,4,5-trichlorophenyl)hydantoin
5-(benzoyl) (ethoxycarbonyl)methylene-3-(p-anisyl)hydantoin
5-(benzoyl) (ethoxycarbonyl)methylene-3-(2-methoxy-4-nitrophenyl)hydantoin
5-(benzoyl) (isopropoxycarbonyl)methylene-3-methylhydantoin
5-(benzoyl) (isopropoxycarbonyl)methylene-3-benzylhydantoin
5-(benzoyl) (isopropoxycarbonyl)methylene-3-(3,5-dichlorophenyl)hydantoin
5-(benzoyl) (isopropoxycarbonyl)methylene-3-(p-anisyl)hydantoin
5-(acetyl) (ethoxycarbonyl)methylene-3-ethylhydantoin
5-(acetyl) (ethoxycarbonyl)methylene-3-phenylhydantoin
5-(acetyl) (ethoxycarbonyl)methylene-3-(p-tolyl)hydantoin
5-(acetyl) (ethoxycarbonyl)methylene-3-(p-chlorophenyl)hydantoin
5-(acetyl) (ethoxycarbonyl)methylene-3-(3,5-dichlorophenyl)hydantoin
5-(acetyl) (isopropoxycarbonyl)methylene-3-methylhydantoin
5-(acetyl) (isopropoxycarbonyl)methylene-3-(n-butyl)hydantoin
5-(acetyl) (isopropoxycarbonyl)methylene-3-(p-tolyl)hydantoin
5-(acetyl) (isopropoxycarbonyl)methylene-3-(3,5-dichlorophenyl)hydantoin
5-(acetyl) (isopropoxycarbonyl)methylene-3-(p-anisyl)hydantoin
5-(cyano) (ethoxycarbonyl)methylene-3-isopropylhydantoin
5-(cyano) (ethoxycarbonyl)methylene-3-allylhydantoin
5-(cyano) (ethoxycarbonyl)methylene-3-cyclohexylhydantoin
5-(cyano) (ethoxycarbonyl)methylene-3-phenylhydantoin
5-(cyano) (ethoxycarbonyl)methylene-3-(p-tolyl)hydantoin
5-(cyano) (ethoxycarbonyl)methylene-3-(3,5-dichlorophenyl)hydantoin
5-(cyano) (methoxycarbonyl)methylene-3-isopropylhydantoin
5-(cyano) (methoxycarbonyl)methylene-3-benzylhydantoin
5-(cyano) (methoxycarbonyl)methylene-3-(3,4-xylyl)hydantoin
5-(cyano) (methoxycarbonyl)methylene-3-(3,5-dichlorophenyl)hydantoin
5-(cyano) (methoxycarbonyl)methylene-3-(2-methoxy-4-nitrophenyl)hydantoin
5-bis(acetyl)methylene-3-ethylhydantoin
5-bis(acetyl)methylene-3-allylhydantoin
5-bis(acetyl)methylene-3-benzylhydantoin
5-bis(acetyl)methylene-3-phenylhydantoin
5-bis(acetyl)methylene-3-(3,5-dichlorophenyl)hydantoin
5-bis(acetyl)methylene-3-(p-anisyl)hydantoin
5-(benzoyl) (ethoxycarbonyl)methylenehydantoin.

3. The hydantoin derivative as claimed in claim 1, which is selected from the group consisting of:
5-bis(ethoxycarbonyl)methylene-3-isopropylhydantoin
5-bis(ethoxycarbonyl)methylene-3-allylhydantoin
5-bis(ethoxycarbonyl)methylene-3-cyclohexylhydantoin
5-bis(ethoxycarbonyl)methylene-3-benzylhydantoin
5-bis(ethoxycarbonyl)methylene-3-phenylhydantoin
5-bis(ethoxycarbonyl)methylene-3-(p-chlorophenyl)hydantoin
5-bis(ethoxycarbonyl)methylene-3-(2-methoxy-4-nitrophenyl)hydantoin
5-bis(methoxycarbonyl)methylene-3-(p-anisyl)hydantoin
5-(benzoyl) (ethoxycarbonyl)methylene-3-(n-butyl)hydantoin
5-(benzoyl) (ethoxycarbonyl)methylene-3-allylhydantoin
5-(benzoyl) (ethoxycarbonyl)methylene-3-cyclohexylhydantoin
5-(benzoyl) (ethoxycarbonyl)methylene-3-(p-tolyl)hydantoin
5-(benzoyl) (ethoxycarbonyl)methylene-3-(2,4,5-trichlorophenyl)hydantoin
5-(acetyl) (ethoxycarbonyl)methylene-3-ethylhydantoin
5-(acetyl) (ethoxycarbonyl)methylene-3-phenylhydantoin
5-(cyano) (ethoxycarbonyl)methylene-3-isopropylhydantoin
5-(cyano) (ethoxycarbonyl)methylene-3-allylhydantoin
5-(cyano) (ethoxycarbonyl)methylene-3-cyclohexylhydantoin
5-(cyano) (ethoxycarbonyl)methylene-3-phenylhydantoin
5-(cyano) (methoxycarbonyl)methylene-3-benzylhydantoin
5-(cyano) (methoxycarbonyl)methylene-3-(2-methoxy-4-nitrophenyl)hydantoin
5-bis(acetyl)methylene-3-ethylhydantoin
5-bis(acetyl)methylene-3-allylhydantoin
5-bis(acetyl)methylene-3-benzylhydantoin
5-bis(acetyl)methylene-3-phenylhydantoin
5-bis(acetyl)methylene-3-(p-anisyl)hydantoin
5-(benzoyl) (ethoxycarbonyl)methylenehydantoin.

4. The hydantoin derivative as claimed in claim 1, which is selected from the group consisting of:
5-bis(ethoxycarbonyl)methylene-3-(n-butyl)hydantoin
5-bis(ethoxycarbonyl)methylene-3-(2,5-dichlorophenyl)hydantoin
5-bis(ethoxycarbonyl)methylene-3-(2-methoxy-4-nitrophenyl)hydantoin
5-bis(methoxycarbonyl)methylene-3-benzylhydantoin
5-bis(methoxycarbonyl)methylene-3-(3,5-dichlorophenyl)hydantoin 5-(benzoyl) (ethoxycarbonyl)methylene-3-allylhydantoin
5(benzoyl) (ethoxycarbonyl)methylene-3-cyclohexylhydantoin
5-(benzoyl) (ethoxycarbonyl)methylene-3-(3,4-xylyl)-hydantoin
5-(benzoyl) (ethoxycarbonyl)methylene-3-(3,5-dichlorophenyl)hydantoin
5-(benzoyl) (isopropoxycarbonyl)methylene-3-methylhydantoin
5-(benzoyl) (isopropoxycarbonyl)methylene-3-benzylhydantoin
5-(benzoyl) (isopropoxycarbonyl)methylene-3-(3,5-dichlorophenyl)hydantoin
5-(benzoyl) (isopropoxycarbonyl)methylene-3-(p-anisyl)hydantoin
5-(acetyl) (ethoxycarbonyl)methylene-3-(3,5-dichlorophenyl)hydantoin
5-(acetyl) (isopropoxycarbonyl)methylene-3-(n-butyl)-hydantoin
5-(acetyl) (isopropoxycarbonyl)methylene-3-(3,5-dichlorophenyl)hydantoin
5-(cyano) (ethoxycarbonyl)methylene-3-allylhydantoin
5-(cyano) (ethoxycarbonyl)methylene-3-cyclohexylhydantoin
5-(cyano) (ethoxycarbonyl)methylene-3-phenylhydantoin
5-(cyano) (methoxycarbonyl)methylene-3-isopropylhydantoin
5-(cyano) (methoxycarbonyl)methylene-3-(3,4-xylyl)-hydantoin
5-bis(acetyl)methylene-3-ethylhydantoin
5-bis(acetyl)methylene-3-benzylhydantoin
5-bis(acetyl)methylene-3-(3,5-dichlorophenyl)hydantoin.

* * * * *